US009826936B2

(12) United States Patent
Rosenshein

(10) Patent No.: US 9,826,936 B2
(45) Date of Patent: Nov. 28, 2017

(54) BODY CAVITY PHYSIOLOGICAL MEASUREMENT DEVICE

(71) Applicant: Beth Rosenshein, Superior, CO (US)

(72) Inventor: Beth Rosenshein, Superior, CO (US)

(*) Notice: Subject to any disclaimer, the term of this patent is extended or adjusted under 35 U.S.C. 154(b) by 0 days.

(21) Appl. No.: 14/678,220

(22) Filed: Apr. 3, 2015

(65) Prior Publication Data

US 2015/0282763 A1    Oct. 8, 2015

Related U.S. Application Data

(60) Provisional application No. 61/974,513, filed on Apr. 3, 2014.

(51) Int. Cl.
| | | |
|---|---|---|
| *A61B 5/00* | (2006.01) | |
| *A61B 5/11* | (2006.01) | |
| *A61B 5/1455* | (2006.01) | |
| *A61B 5/01* | (2006.01) | |

(52) U.S. Cl.
CPC .......... *A61B 5/6867* (2013.01); *A61B 5/0002* (2013.01); *A61B 5/0031* (2013.01); *A61B 5/015* (2013.01); *A61B 5/1107* (2013.01); *A61B 5/1121* (2013.01); *A61B 5/14551* (2013.01); *A61B 5/4331* (2013.01)

(58) Field of Classification Search
CPC ... A61B 5/1076; A61B 5/6867; A61B 5/1107; A61B 5/1121
See application file for complete search history.

(56) References Cited

U.S. PATENT DOCUMENTS

| | | | |
|---|---|---|---|
| 3,983,874 A | 10/1976 | Davis et al. | |
| 4,526,578 A | 7/1985 | Wong | |
| 4,696,294 A | 9/1987 | Reyner | |
| 4,757,823 A | 7/1988 | Hofmeister et al. | |
| 5,044,376 A | 9/1991 | Shields | |
| 5,222,485 A | 6/1993 | Jerath | |
| 5,851,188 A | 12/1998 | Bullard et al. | |
| 6,039,701 A | 3/2000 | Sliwa et al. | |
| 6,363,271 B1 | 3/2002 | Berry | |
| 6,383,137 B1* | 5/2002 | Berry .................. | A61B 5/1076 600/304 |
| 7,128,706 B2* | 10/2006 | Morgenstern ...... | A61B 5/04882 600/30 |
| 7,314,453 B2 | 1/2008 | Kuo | |
| 7,460,896 B2 | 12/2008 | Iddan | |
| 2004/0064133 A1 | 4/2004 | Miller et al. | |
| 2005/0245795 A1 | 11/2005 | Good et al. | |

(Continued)

FOREIGN PATENT DOCUMENTS

WO    2008130467    10/2008

*Primary Examiner* — Michael D Abreu
(74) *Attorney, Agent, or Firm* — Russell T. Manning; Marsh Fischmann & Breyfogle LLP

(57) ABSTRACT

Provided herein is a self-contained physiological measuring device adapted for disposition within a patient body cavity, primarily the vagina, for an extended period of time (e.g., 6-48 hours or more). While disposed within the body cavity, the device periodically measures one or more physiological parameters at known locations within the body cavity. In addition to measuring such physiological parameters, the device is operative to store such measurements to memory for subsequent download/processing upon removal of the device from the body cavity and/or upon wireless interrogation.

15 Claims, 14 Drawing Sheets

(56) References Cited

U.S. PATENT DOCUMENTS

2006/0084848 A1   4/2006  Mitchnick
2009/0281397 A1   11/2009 Lavoisier
2010/0094270 A1*  4/2010  Sharma .................. A61B 18/04
                                               606/27

* cited by examiner

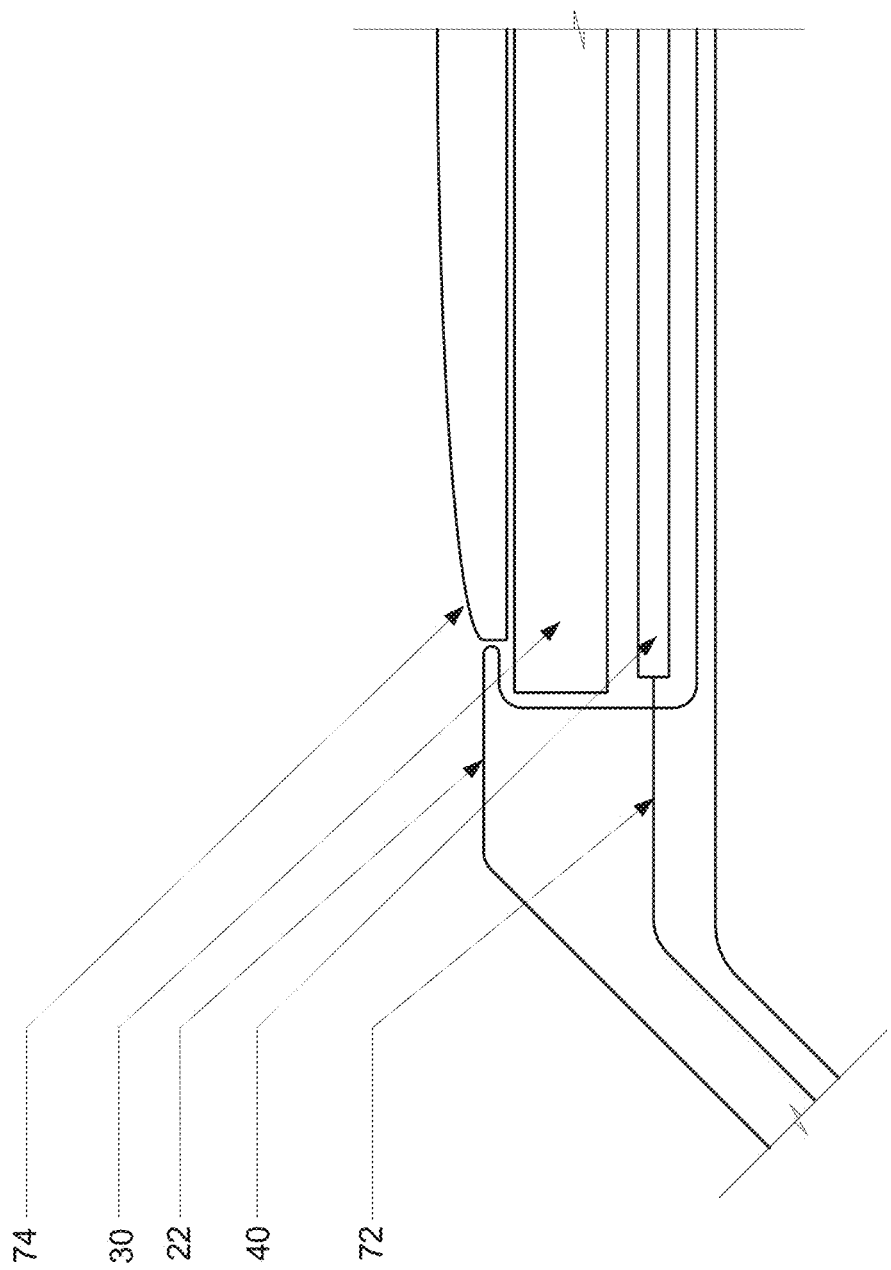

BODY CAVITY PHYSIOLOGICAL MEASUREMENT DEVICE

CROSS REFERENCE

The present application claims the benefit of U.S. Provisional Application No. 61/974,513 having a filing date of Apr. 3, 2014, the entire contents of which is incorporated herein by reference.

FIELD

The presented inventions are directed to a method and system for monitoring one or more physiological parameters over an extended period of time. One aspect is directed to a self-contained physiological monitoring device for disposition within a body cavity to make physiological measurements over an extended period of time. A further aspect is directed to the mapping of physiological measurements to internal tissue locations of the body cavity based on an identified orientation of the self-contained monitoring device.

BACKGROUND

There are many different situations in which non-invasive monitoring of a human subject (e.g., patient) is desired. For example, such monitoring may be useful as part of the overall health maintenance of the patient, and could be used in order to diagnose a physiological condition and/or detect a deterioration in the physiological condition of the patient. Likewise, the option of monitoring physiological condition via a remote, non-invasive means has promise for improving access to and enhancing the delivery of treatment for an identified physiological condition. Numerous non-invasive sensors exist for monitoring one or more physiological conditions. For instance, chest straps are known for monitoring heart rate. Pulse oximeters non-invasively monitor, inter alia, blood oxygenation. However, difficulties arise when a desired physiological parameter is within a body cavity (e.g., vagina) of the patient. In such a situation, a monitoring device must reside within the body cavity and collect desired parameters.

Various prior devices have been proposed for use in monitoring one or more intravaginal physiological parameters. For instance, U.S. Patent Application 2006/0084848 is directed to an intravaginal device that monitors temperature, oxygenation and/or movement of a patient/wearer of the device. While previous devices have identified the desirability of monitoring one or more intravaginal physiological parameters, such fail to provide information regarding where measurements are taken within the vagina or to provide measurements of multiple locations within the vagina. Stated otherwise, such prior devices assume uniform physiological parameters exist throughout the vagina.

SUMMARY

Provided herein is a self-contained physiological measuring device adapted for disposition within a patient body cavity (e.g., the vagina) for an extended period of time (e.g., 6-48 hours or more). While disposed within the body cavity, the device periodically measures one or more physiological parameters at multiple locations. The device is annular or toroid in shape similar to a diaphragm. Importantly, the device is operative to utilize outputs from one or more motion sensors (e.g., accelerometers) to determine the orientation of the annular device within the body cavity. That is, the angular orientation of the annular device relative to the body cavity may be determined. This allows for identifying approximately where each physiological measurement is taken within the body cavity. Further, if the device is utilized at different temporal points, subsequent measurements of a physiological parameter of a specific tissue location may be compared to prior measurements for that location. Yet further, identification of the location of the physiological parameter(s) allows for comparison of that parameter with baseline values for a specific region of the body cavity. Stated otherwise, the ability to determine the orientation of the device allows mapping measurements from sensors having a known location on the device to internal locations of the body cavity. The device allows mapping information to locations within the vaginal cavity.

In addition to measuring physiological parameters at multiple locations, the device is operative to store such measurements to memory for subsequent download/processing upon removal of the device from the body cavity and/or upon wireless interrogation. Generally the device utilizes passive sensing means to measure one or more parameters while positioned within the body cavity. In this regard, the device is non-invasive in that, while utilized internally, the sensors do not penetrate patient tissue. Therefore, while being utilized internally the device is considered non-invasive.

Generally, the device includes an on-board power supply (e.g., battery), a memory device (e.g., EEPROM or other computer readable media), one or more sets of sensors disposed at known spaced locations about the annular/toroidal body of the device for taking various measurements, and circuitry for controlling the operation of the device. Such circuitry may include firmware, hardware, computer readable memory, software and/or processing capabilities (e.g., a microprocessor or micro-controller). The device is operative to take measurements at predetermine intervals and store such measurements to the memory. Such information may be retrieved from the memory (e.g., upon removal from the body cavity) utilizing either direct interconnection or wireless data transfer. In the latter regard, the device may include a wireless interface (e.g., Bluetooth, RFI, etc.) that allows for transferring data from the memory to an external processing platform (e.g., CPU) for processing and diagnosis purposes. Likewise, the wireless interface may permit programming the device.

The sensors/sensor sets of the device may be any sensors that are deemed appropriate for a particular diagnostic purpose. Such sensors may include, without limitation, strain gauges, pH sensors, pulse oximetry sensors (e.g., LEDs, photo detectors, etc.), temperature sensors, etc. It will be appreciated that strain gauges may be utilized to monitor constriction over time, which may identify, for example, vasoconstriction and vasodilation. A pulse oximetry sensor may determine inter alia, oxygen and/or $CO_2$ levels. Furthermore, information from one or more of the sensors may be utilized to infer additional physiological parameters including, without limitation, pH, pOH etc.

As noted, the device also includes multiple motion sensors and typically at least three motion sensors disposed at spaced locations about its annular/toroidal body. Such motion sensors generate outputs that collectively allow for determining an orientation of the body of the device. For instance, in a vaginal application, the vaginal cavity will have an expected plane where the annular/toroidal body device will be positioned, when a user is in a predetermined position. By way of example, when a user is lying of their back, a plane of the vaginal vault is disposed at an angle of approximately 45° extending from a lower point proximate to the posterior fornix of the cervix to an upper point proximate to the anterior fornix of the cervix. By assuming the annular/toroidal body of the device is disposed in this plane, a portion of the device determined to be the lowest may be determined to be positioned proximate to the posterior fornix in the vaginal vault/cul-de-sac (e.g., proximate to the colon). In such a situation, the most upright portion of the device may be determined to be positioned proximate to the anterior fornix in the vaginal vault (e.g., proximate to the bladder). It will be appreciated that other expected planes may be utilized when the user is in different positions. Accordingly, the position of sensors/sensor sets, disposed about the annular/toroidal body of the device, relative to the body cavity may be inferred.

In addition to allowing for identifying the orientation of the device within the body cavity, the motion sensors allow for identifying the origin of spasms/contractions. For instance, in a vaginal application, contractions may induce movement in the motion sensors. Further, motion sensors more proximally located to the source of movement will identify movement before more distally located motion sensors. In this regard, contractions may be identified as originating in, for example, the colon, the uterus or bladder based on the outputs of the motion sensors.

It will be appreciated that the device may include additional components as well. Such components may include rectifying circuitry that allows for receiving and/or storing energy wirelessly (e.g., from an RF field or a magnetic induction field) while the device is within the body cavity or not. In other embodiments, the device may provide information from the memory while located in the body cavity. That is, the device may include a transmitter that is operative to transmit information wirelessly to an external device. However, this is not a requirement.

The sensors and accelerometers of the device are disposed on an annular body, which is adapted for insertion into a body cavity. In one arrangement, the annular body is pliable to allow the device to at least partially deform when inserted through a patient orifice. It may be desirable that the components of the device interconnected to the body are sealed to prevent the intrusion of body fluids. In one arrangement, these components may be encased in a non-permeable material. Such materials may include, without limitation, medical grade silicone. To permit use of a pulse oximetry sensor, it may be desirable that the encasing material be translucent.

To allow for mapping different regions of the body cavity, multiple sensor sets are typically spaced about the annular body. For instance, between three and 15 sets of sensors may be angularly spaced about the body. In this regard, physiological parameters may be monitored at multiple locations around the annular body to provide improved parameter monitoring. In one arrangement, multiple pulse oximeter sensors are disposed about the annular body. This may allow for identifying regions within the body cavity having, for instance, lower blood oxygen levels. This may allow for directing treatment to a location that has impaired blood flow. In another arrangement, multiple pressure sensors are disposed about the annular body. Such pressure sensors may be utilized, inter alia, to identify areas of swelling.

The self-contained measurement device may be utilized in a number of monitoring situations. Such measurements may be utilized for diagnosis of gonadal dysfunction and/or failure in female patients. In women, gonadal dysfunction and/or failure is the failure of the ovaries to produce adequate ovarian hormones. During such ovarian dysfunction and/or failure, some or all of the ovarian hormones are below normal level which raises the risk of a number of different illnesses. Such dysfunction and/or failure is also known as hypogonadism. Women suffering from hypogonadism are at risk for osteoporosis, breast cancer, heart disease, periodontal disease and diminished cognitive abilities. Accordingly, it is desirable to monitor patients for decreased ovarian hormone outputs such that hormone replacement therapy can be initiated and/or properly dosed. Further, the ability to identify different locations within the vagina having different hormone levels may allow for directing treatment to a particular location The vaginal device allows for monitoring physiological parameters associated with such hormones over an extended period of time. In one arrangement, the vaginal device is worn between 6-48 hours with monitoring taking place every one to five seconds (or other periodic schedule) wherein the device measures oxygen, carbon dioxide, strain/pressure, temperature, and/or other parameters. This information may be subsequently downloaded upon removal of the device for subsequent processing and analysis.

In a related aspect, the device is utilized to generate baseline values (e.g., diagnostic markers) that may be applicable to diagnosis of one or more therapeutic conditions, including but not limited to hypogonadism. In this aspect, a plurality of patients may utilize the device over an extended period to obtain generate a map relative to a vaginal vault of one or more parameters of a sample group. Such sample groups may be selected based on, for example, age, ethnicity, and/or the presence or absence of a medical condition. In any arrangement, the sample group of patients utilizes the device internally for a predetermined period of time during which the device takes periodic measurements of one or more physiological parameters at one or more internal locations. Such parameters may include, without limitation, pulse rate, blood oxygen and/or carbon dioxide levels, strain levels (e.g. constriction), temperature, etc. It will be appreciated that such measurements may be direct measurements or may be inferred or calculated during processing after removal of the device or downloading of information from the device. At the end of the set monitoring period, information from multiple patients is gathered to establish baseline characteristic maps for the sample group. Such baseline characteristic maps may be determined by various known processing techniques. Such known processing techniques may include, for example, regression analysis (or other analysis) to identify the relationship of one or more therapeutic conditions (e.g., hormone levels) to one or more physiological measurements obtained by the device. It will be further appreciated that multiple different physiological measurements may be utilized in conjunction to establish correspondences with one or more therapeutic conditions. For instance, such baseline measurements may be a combination of strain and oxygen saturation levels or other values (e.g., pH levels). Such analysis may determine baseline values or calibrations for the sample group.

In a further arrangement, first and second or multiple sample groups may be monitored to identify differences between these groups. For instance, a control group may comprise one or more individuals that do not have a particular therapeutic condition. In contrast, one or more test groups may comprise one or more individuals having a particular therapeutic condition. Accordingly, analysis of physiological measurements collected from each of these groups may be gathered and processed to identify differences in the measured values between the groups. Accordingly, such differences in the measured values may subsequently be utilized by, for example, physicians to identify a therapeutic condition and/or the degree of such a therapeutic condition. That is, after such clinical trials, baselines or diagnostic markers may be established for one or more particular therapeutic conditions. Accordingly, a user may wear the device for a predetermined time to non-invasively monitor one or more physiological parameters and these measured parameters may be compared to the established baselines to identify the presence, absence and/or degree of a medical condition. Likewise, therapeutic treatment may be established based on such identification.

In another aspect, the self-contained device may also administer one or more therapeutic agents. To administer such agents, the device includes one or more reservoirs (e.g., spaced about the annular/toroidal body) that contain a liquefied or solid therapeutic agent(s). Such reservoirs may be pressurized such that, upon opening the reservoir, the liquefied or solid therapeutic agent is expelled. For instance, the reservoir may form an elastic bladder that stretches when filled with the therapeutic agent. Alternatively, the device may include an actuator to expel the therapeutic agent from the reservoirs. In such an arrangement, the reservoir may include, for example, a plunger that moves in response to an applied signal from the device controller. Other actuators that may be utilized include, without limitation, thin film actuators and micro-pumps. Knowledge of the orientation of the annular/toroidal body of the device may allow administering an agent to a focused region of the vaginal vault.

Typically, when including a reservoir, the device will also include a valve or other means for selectively maintaining the therapeutic agent within the reservoir prior to desired administration. In such an arrangement, the controller may generate a control signal to actuate a valve opening the reservoir or otherwise permitting the therapeutic agent to be displaced from the reservoir. In a further arrangement, the device may include multiple reservoirs. This may allow for providing periodic doses of a therapeutic agent.

BRIEF DESCRIPTION OF THE FIGURES

FIG. 4 illustrates a partial cross-sectional view of the control module of the device.

DETAILED DESCRIPTION

Disclosed herein is a system and method (i.e., utility) for monitoring patient physiological parameters. The utility utilizes a self-contained measurement/sensing device that is designed for placement within a body cavity (e.g., the vagina). The device includes an onboard power source(s), sensors and an electronic memory for storing physiological measurements taken by one or more of the sensors.

Figure 1:
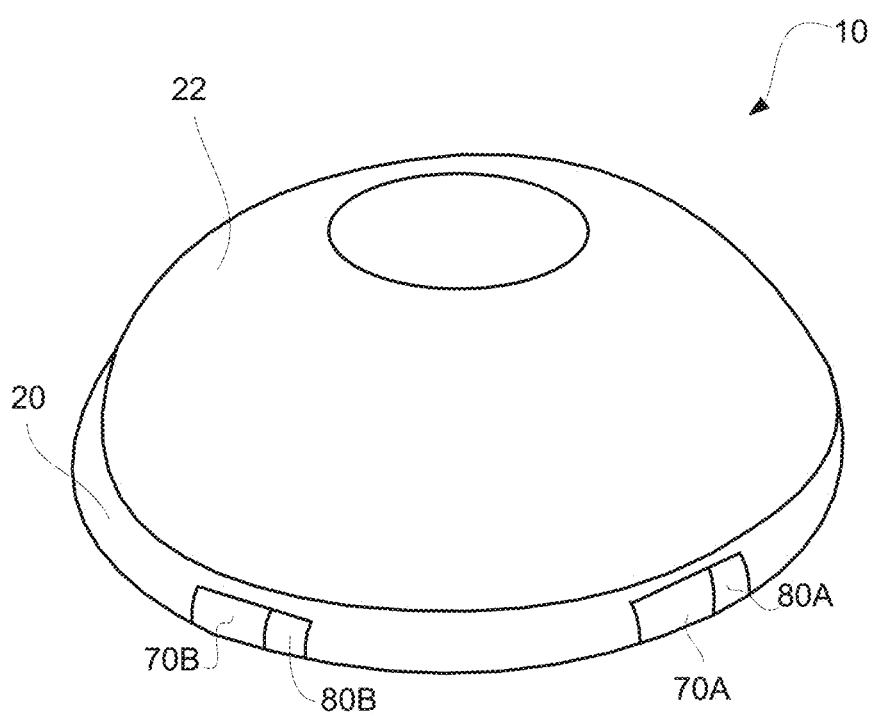
FIG. 1 illustrates an elevated view of the device.
Figure 2:
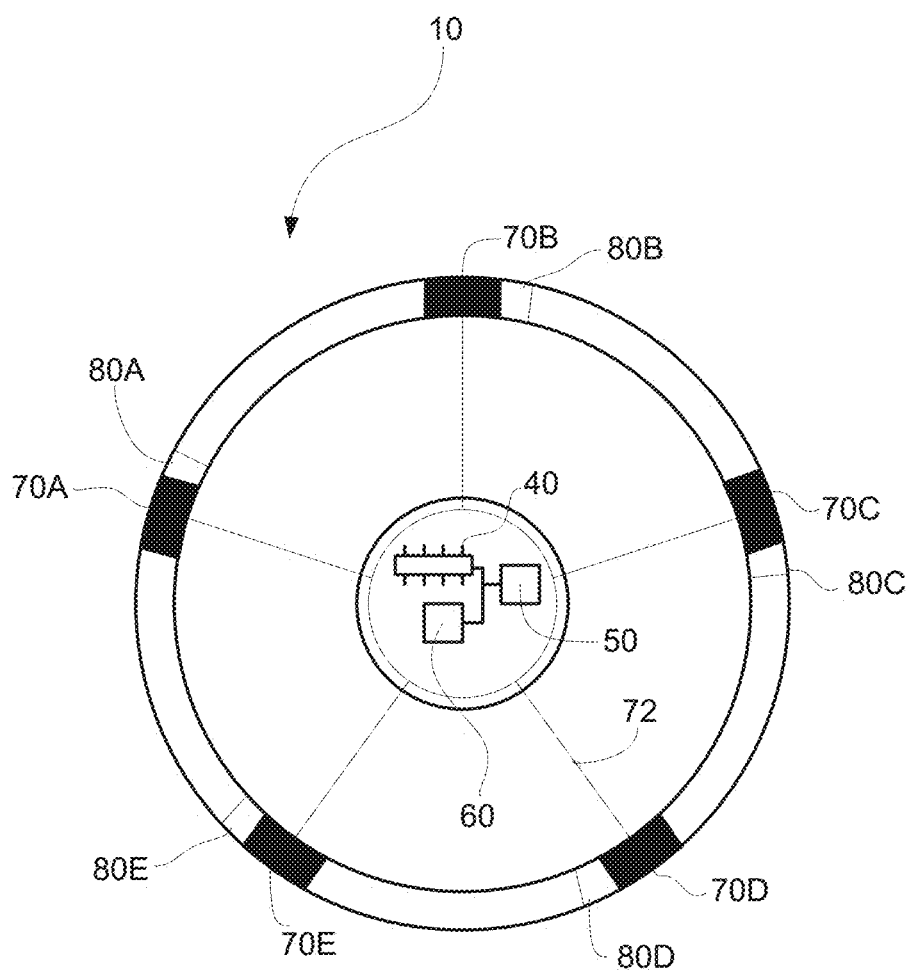
FIG. 2 illustrates a bottom view of the device.

FIGS. 1 and 2 illustrate one embodiment of a self-contained measurement device that is adapted for vaginal insertion. As shown, the device is formed in a manner that is similar to that of a vaginal diaphragm. In this regard, the device 10 includes an annular ring/toroid or body 20. Generally, the annular body 20 is made from a spring metal or plastic and is coated with a flexible, non-toxic, vaginally acceptable material. Such materials may include silicone rubber or other medical grade silicones. The annular body 20 forms a body of the device that supports the measuring/sensory components discussed herein. The annular body 20 is shaped and adapted to fit snuggly in the vaginal vault between the posterior aspect of the pubis and the cul-de-sac. See FIG. 3B. The annular body may be generally circular, oval, or other shapes suitably shaped and adapted for placement in the vaginal cul-de-sac, posterior and anterior to the cervix. Generally, the annular body will have a diameter between about 50 mm and 80 mm. The size of the annular body may be varied to accommodate different individuals.

In the present embodiment, a dome 22 extends about the periphery of the annular body 20. This dome 22 may be closed and in the present embodiment supports a plurality of electrical components that provide the sensing and/or measurement function described herein. These components generally include a power source 30 (See FIG. 4), electrical circuitry/control module 40, communications circuitry 50, and memory 60. The annular body supports multiple sets of sensors 70A-N (hereafter 70 unless specifically referenced) and multiple motion sensors 80A-N (e.g., accelerometers; hereafter 80 unless specifically referenced) at different angular locations. The sensor sets 70 and motion sensors 80 are illustrates as being co-located. However, this is not a requirement. The various electrical components 30-80 are interconnected by a flexible circuit 32. Furthermore, the flexible circuit 32 may electrically connect the sensor sets 70 and/or motion sensors 80 to the control module 40 via wiring 72 that extends through the dome 22.

The illustrated embodiment includes five sensor sets 70 and five motion sensors 80 disposed about the periphery of the annular body 20. However, it will be appreciated that more or fewer of these components may be utilized. For instance as few as three or as many as 15-20 may be incorporated. Use of an increased number of sensor sets 70 allows for more detailed mapping of physiological conditions within the body cavity.

The plurality of motion sensors 80 are disposed at multiple angular locations about the annular body 20. These motion sensors (e.g. accelerometers) generate a motion output. This motion output typically defines a vector having one or more axes. This information is utilized to determine the angular orientation of the annular body 20 of the device relative to the vaginal vault of a user. In order to get rotational information/angular orientation from the accelerometers, the device utilizes an initial calibration period. After inserting the ring, the user either stand ups or lies flat and remain still for a predetermined period of time (e.g., 2-3 minutes). Given the acceleration vectors from each of the motion sensors 80 and their known physical position and orientation relative to the center of the annular body 20 in the plane of the body (2D space), their 3D positions are calculated relative to the center of the ring (3 points 3 and unknowns, 5 point and 5 unknowns etc.) based on an approximate known plane of a woman's physiology, when in a known position. The planes of the annular body 20 and the approximate known plane of the user are compared to determine the relative positions and angular orientation of the annular body 20.

Figure 3A:
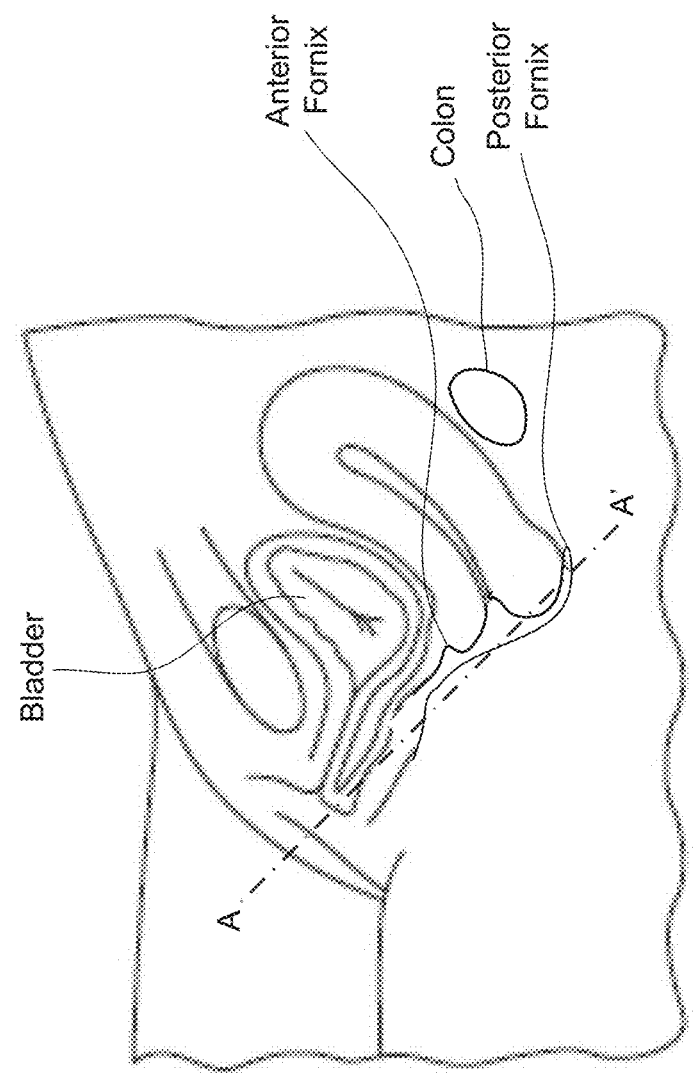
FIG. 3A illustrates a known plane of a vaginal cavity.
Figure 3B:
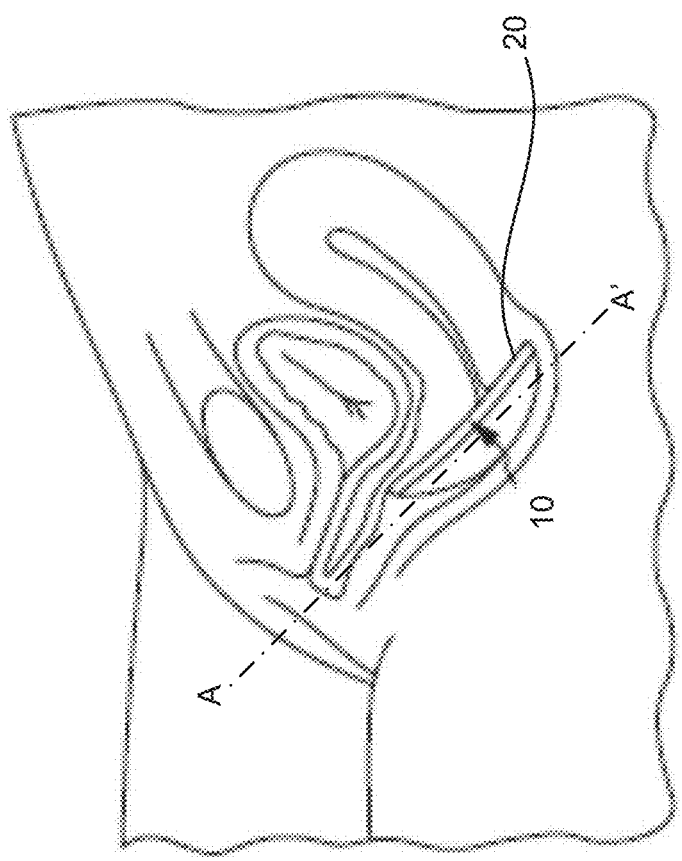
FIG. 3B illustrates the device in the vaginal cavity.
Figure 3C:
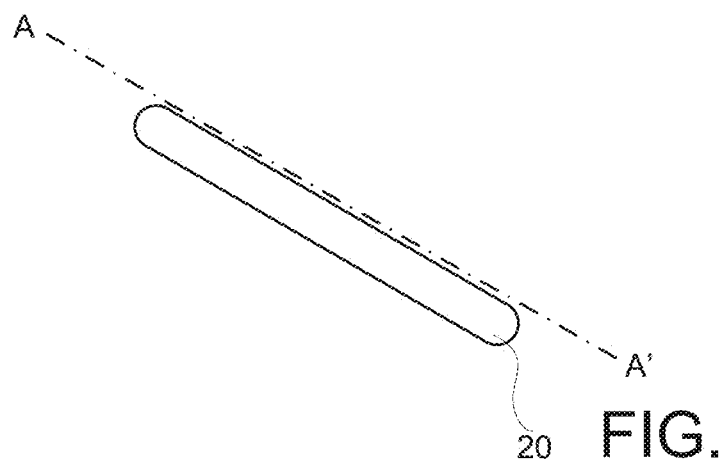
FIG. 3C illustrates a side view of the device relative to the known plane.

Determination of the angular orientation is more fully described in FIGS. 3A-3D. Referring to FIG. 3A, the user initially assumes a known position, which in the illustrated embodiment is on her back. As shown, when a user is lying on their back, an expected plane A-A' of the vaginal vault is disposed at an angle of approximately 45° extending from a lower point proximate to the posterior fornix to an upper point proximate to the anterior fornix. When the device 10 is inserted into the vaginal vault, the annular body 20 is positioned in the posterior fornix and anterior fornix as illustrated in FIG. 3B. Accordingly, the plane defined by annular body 20 is substantially parallel or coplanar with the expected plane A-A' of the user as shown by the side and bottom views of FIGS. 3C and 3D, respectively. When the annular body 20 of the device 10 is disposed in or parallel to this plane A-A', the lowest portion of the device may be determined to be positioned proximate to the posterior fornix (e.g., proximate to the colon). In such a situation, the most upright portion of the device 10 may be determined to be positioned proximate to the anterior fornix (e.g., proximate to the bladder). That is, the outputs of the motion sensors 80 are processed to determine the orientation of the device 10. As the location of the sensor sets 70 are known relative to the motion sensors and the annular body, a determination of the relative location of the sensor sets 70 to the vaginal vault may be determine. For instance, in the illustrated embodiment, sensor set 70C may be determined as the sensor set closest to the colon and sensor set 70A may be determined as the sensor set closest to the bladder. Accordingly, physiological parameters monitored by these sensor sets may be 'mapped' to these locations and/or compared with baseline values for these locations.

As shown in FIG. 2, the control module 40 includes an integrated chip having various firmware defined therein. Furthermore, it would be appreciated that the control module 40 may be programmable to perform functionality required by different measurement sensors variously incorporated into the device. That is, the control module manages the overall device operations. Such device operations typically reside in a computer readable memory as computer instructions (e.g., embedded software). The power source 30 overlays and powers the control module 40 and the other active components of the device 10. In one embodiment, the control module 40 is in operative communication with a wireless transceiver 50, in this case a Bluetooth transceiver. The transceiver is operative to send and/or receive wireless signals via an antenna 74 for downloading data to a remote computer and/or uploading instructions. Typically, such uploading and downloading will be performed once the device 10 is removed from the body. However, in other embodiments it may be possible and/or desirable to provide wireless transmission while the device is disposed within the body. In one arrangement, the wireless transceiver 50 may further include rectifying circuitry such that power may be provided to the device 10 wirelessly. However, this is not a requirement.

The circuitry includes a memory device 60 at least for storing sensor measurements made by the sensors. The memory may also include operating instructions (e.g., computer instructions) for the device. In one embodiment, EEPROM memory is utilized for the device. The memory device may be programmed with, for example, patient information and/or calibration settings for one or more of the sensors. The type and function of memory incorporated into the device may affect the power requirements of the system. That is, different memories may be utilized based on different requirements and/or intended functions of a given sensor.

Figure 5:
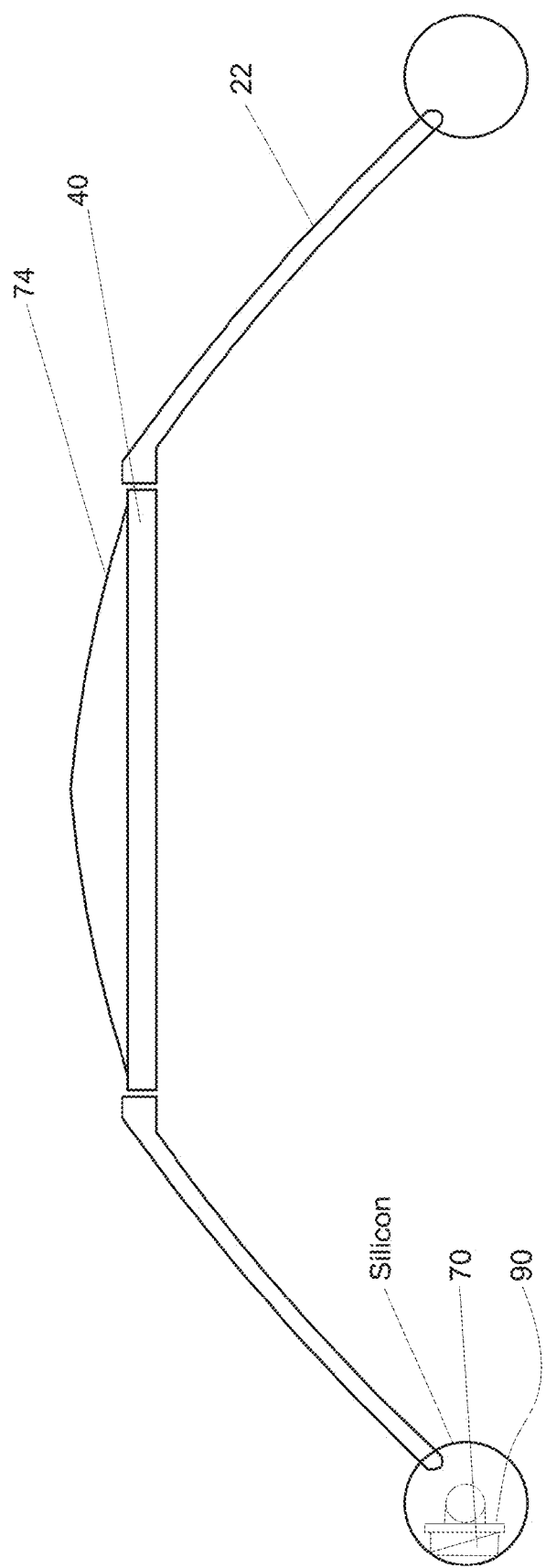
FIG. 5 illustrates a cross-sectional view of the device.
Figure 6:
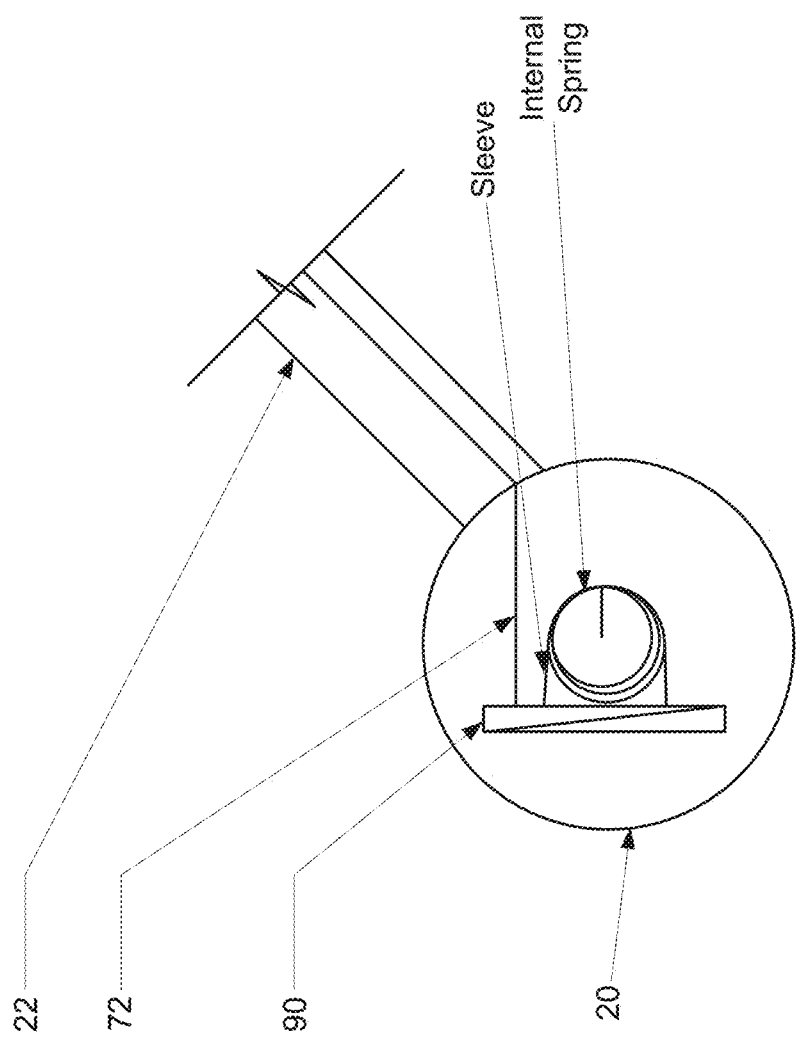
FIG. 6 illustrates a partial cross-sectional view of a sensor set of the device.

FIGS. 5 and 6 show cross sectional views of an alternate embodiment of the device 10. These cross-sectional views extend though one sensor set 70. As illustrated in this embodiment, each sensor set includes an individual circuit board 90, which may be flexible. The various sensors and/or accelerometers may be disposed on this circuit board 90. Accordingly, the circuit board 90 may be connected to the battery and/or antenna via wiring extending into the dome 22.

In one embodiment, each sensor set 70 includes a strain gauge to allow for measuring pressure and/or contraction in the vaginal wall at each of the angular location about the annular body. Such information may be correlated to determine, for example, vasoconstriction over time and/or locations of constriction within the vagina. Each sensor set may also include a temperature measurement device. Such a temperature measurement device may be any element that is operable to provide an output signal indicative of temperature. Such a temperature measurement device may include temperature sensitive resisters (i.e. thermistors) and/or thermocouples. Again, by having multiple sensor sets 70 disposed at different angular locations about the annular body, different temperature measurements may be made for different locations.

In one embodiment, each sensor set 70 may include a pulse oximetry sensor. In this embodiment, the pulse oximetry sensor will typically include first and second light emitting diodes. For instance, the first LED may be a red LED with a wavelength of approximately 660 NM and the other LED may be an infrared sensor having a wavelength between about 900 and 940 NM. It will be appreciated that other wavelengths are possible and within the scope of the present invention. In addition, the pulse oximetry sensor will include a photo detector for receiving reflected light. That is, during operation the first and second LEDs are operative to apply light to patient tissue and the photodetector is operative to receive light reflected back from that tissue. In known methods, the ratio of the absorption of the red and infrared light is related to the oxyhemoglobin and deoxyhemoglobin ratio of the patient. That is, processing the information received from the oximetry sensor may provide an estimate of arterial and venous blood oxygen levels. Other physiological information may be obtained or derived from the oximetry information including heart rate and $CO_2$. Furthermore, use of additional light wavelengths may allow for obtaining measurements of additional characteristics including, without limitation, carbon dioxide. In addition, it will be appreciated that the information from the pulse oximetry sensor may be utilized in conjunction with one or more other measured values and/or calibration values (e.g., in subsequent processing) to infer one or more physiological parameters. Such parameters may include pH, pOH, etc.

It will be appreciated that additional circuitry and/or sensors may be included into the device 10. For instance, the device may include one or more pH sensors that allows for effectively monitoring the pH of the patient. Embodiments that utilize a direct measuring pH sensor may have sensing components in direct contact with body fluids of the patient. That is, one or more electrodes may extend through the biologically inert coating of medical grade silicone, PTFE, high-density polyethylene (HDPE) or the like.

In embodiments where the electrical components of the device do not come into direct contact with the patient bodily fluids, the device may be reusable. That is, the device may be sterilized and reused on a common patient. Alternatively, in other embodiments the device may allow for sterilization (e.g. autoclaving) such the device may be utilized with different patients. Alternatively, the device may be disposable.

Figure 7:
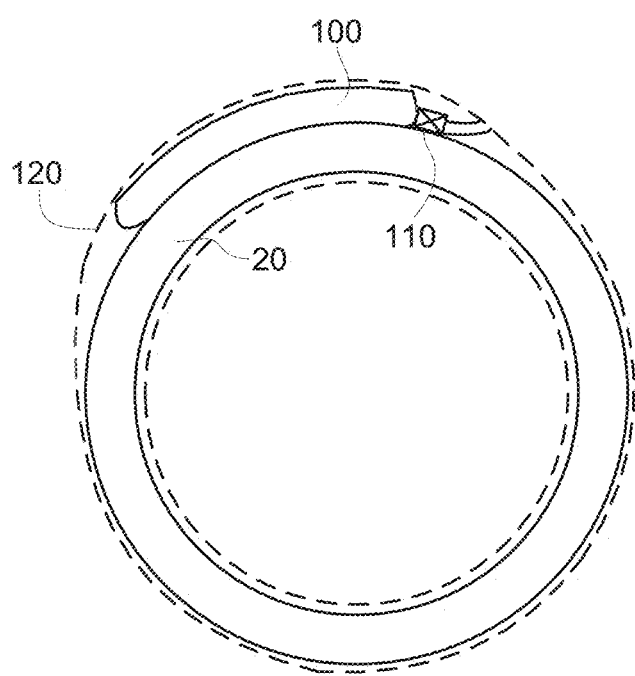
FIG. 7 illustrates incorporation of a reservoir with the device.

FIG. 7 illustrates another embodiment of the device. In this embodiment, the device is operative to apply and deliver one or more therapeutic agents to a user. The device allows for the controlled delivery of therapeutic agents to the cervix and/or vagina. Such therapeutic agents may include, without limitation, local anesthesia prior to endocervix biopsies, antifugals, anti-infectives, treatments for vaginal and cervical dysplasia and cancer, hormonal therapy etc.

As shown, the device 10 includes one or more reservoir chambers 100 (only one show for clarity) disposed about the periphery of the annular body. The reservoir chamber(s) 100 contain one or more therapeutic agents. In one embodiment, the reservoir chamber 100 is made of a flexible and/or elastic material that may be encased within the silicone prior to the insertion of the therapeutic agent therein. Accordingly, upon insertion of the therapeutic agent, the encasing silicone and/or elastic reservoir apply a compressive force to the contents of the reservoir. This compressive force may assist in displacing the agent from the reservoir chamber when opened.

The reservoir further includes a valve 110 for selectively maintaining the therapeutic agent therein. This valve or a conduit extending there from is typically exposed outside of the encasing silicone to permit the therapeutic agent to be administered to the patient. The valve 110 is operatively connected to the control module (not shown), which may selectively actuate the valve to permit the controlled release of the therapeutic agent. In operation, one or more therapeutic agents are delivered to and deposited into the reservoir. A manufacturer may apply the therapeutic agent(s) to the reservoir 100 prior to shipping the device, or medical personnel or the patient may apply the therapeutic agent(s) immediately prior to using the device. As will be appreciated, a reservoir may be included at each of the angular locations of the sensor sets 70. In this regard, upon determining the angular orientation of the device, a reservoir closest to a desired area of application may be utilized to administer an agent. That is, therapeutic agents may be targeted to desired locations.

In another embodiment, the device may include an actuator (e.g., piezoelectric actuator) for physically displacing fluid from a reservoir. In such an arrangement, the reservoir may operate similarly to a syringe or other compressive force. Likewise, the controller may be operative to control the dosage volume and/or administer multiple doses. In other embodiments, the device includes multiple reservoirs to permit multiple doses and/or the administering of multiple therapeutic agents.

Figure 3D:
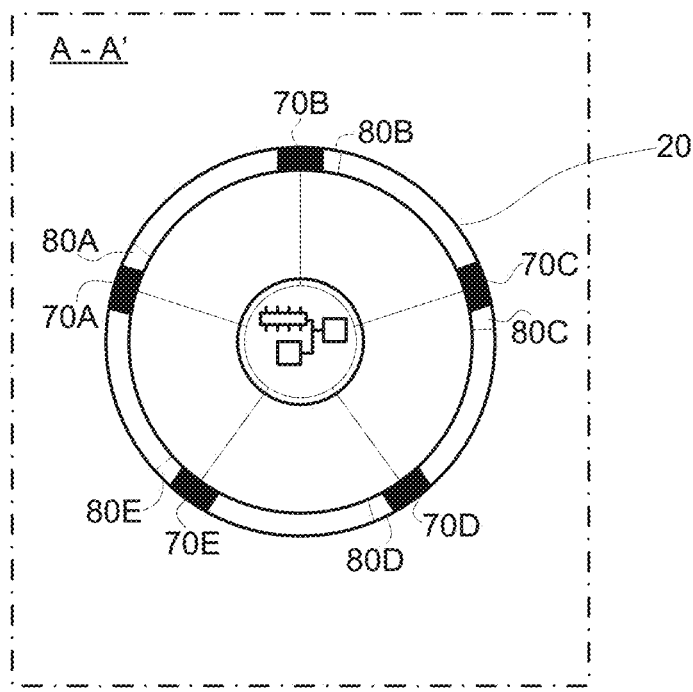
FIG. 3D illustrates a bottom view of the device relative to the known plane.
Figure 8:
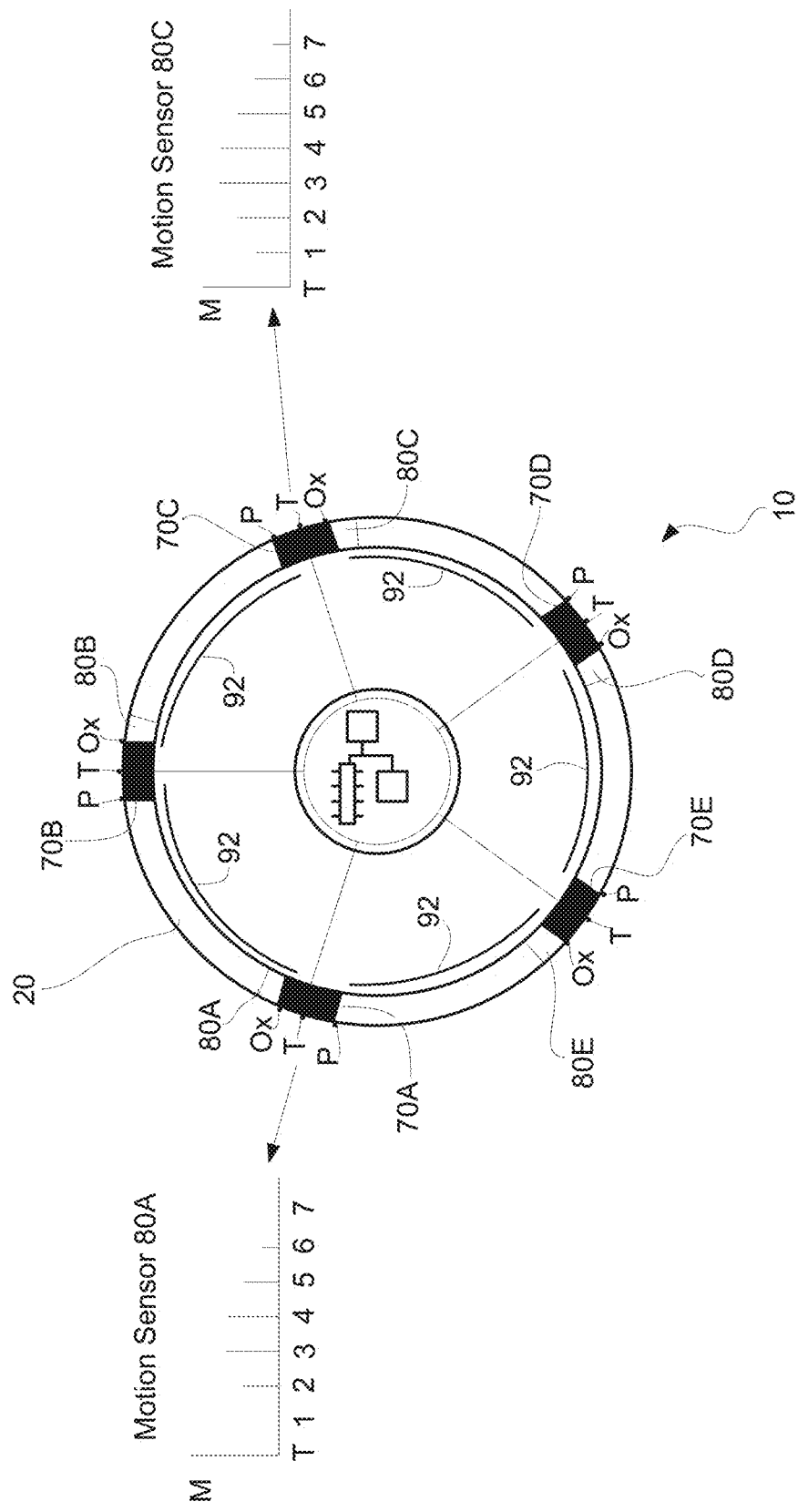
FIG. 8 illustrates outputs of the device while in use.

FIG. 8 illustrates the device 10 of FIG. 3D in use. As shown, the device 10 again includes five sensor sets 70A-70E. In the illustrated embodiment, each sensor set 70 includes a pressure sensor (P), a temperature sensor (T) and a pulse-ox sensor (O). Additionally, the device 10 includes five motion sensors 80A-80E, which in the present embodiment are co-located with the sensor sets 70. During operation, each sensor set 70 is operative to take measurements, which may occur periodically. The following table illustrates a non-limiting exemplary data output of each of the sensor sets 70 and motion sensors 80:

| | |
|---|---|
| Time 1 | (A, $M_1$, $T_1$, $P_1$, $Ox_1$ ... B, $M_1$, $T_1$, $P_1$, $Ox_1$ ... N, $M_1$, $T_1$, $P_1$, $Ox_1$ ... ) |
| Time 2 | (A, $M_2$, $T_2$, $P_2$, $Ox_2$ ... B, $M_2$, $T_2$, $P_2$, $Ox_2$ ... N, $M_2$, $T_2$, $P_2$, $Ox_2$ ... ) |
| Time 3 | (A, $M_3$, $T_2$, $P_3$, $Ox_3$ ... B, $M_3$, $T_3$, $P_3$, $Ox_3$ ... N, $M_3$, $T_3$, $P_3$, $Ox_3$ ... ) |

As shown, at each measurement time (e.g., Time 1, Time 2, etc.) measurements from each of the sensors is recorded. In this regard, a resulting data set for each time period includes for each sensor set 70 and motion sensor 80 (i.e., A-N; depending on the number sensors) a motion sensor output, a temperature output, a pressure output and an oxygen output. The sequence of measurements may be utilized for mapping physiological parameters within the body cavity. For instance, as shown in FIG. 8, the motion outputs of motion sensors 80C and 80A are plotted over time. The remainder of the motion outputs of the other motion sensors may likewise be plotted but are not shown for purposes of clarity.

As discussed above in relation to FIG. 3D, it may be determined from the orientation of the device that motion sensor 80C is located in the posterior portion of the vaginal cavity proximate to the colon of the user while motion sensor 80A is located in the anterior portion of the vaginal cavity proximate to the bladder of the user. As shown, at time T1 motion sensor 80C identifies movement or vibration. In contrast, at time T1 motion sensor 80A does not identify movement or vibration. Motion sensor 80C identifies further movement or vibration during times T2-T7. Motion sensor 80A also identifies corresponding movement during times T2-T6. Based on this information, the origination location of this movement or vibration may be identified. For instance, as motion sensor 80C identifies the movement prior to that movement being identified by motion sensor 80A, it may be inferred that the motion originates from the posterior portion of the vaginal cavity. Further, it will be appreciated that the outputs of the other motion sensors may be further utilized to better identify the origination location of the movement. That is, a combination of the outputs from all the motion sensors may be processed to generate a vector identifying the origination of the motion. For instance, the origination of the motion may be identified as originating in the colon identifying gastrointestinal origination. In other arrangements, such motions may be identified as originating from the bladder (i.e., bladder spasms).

Figure 9A:
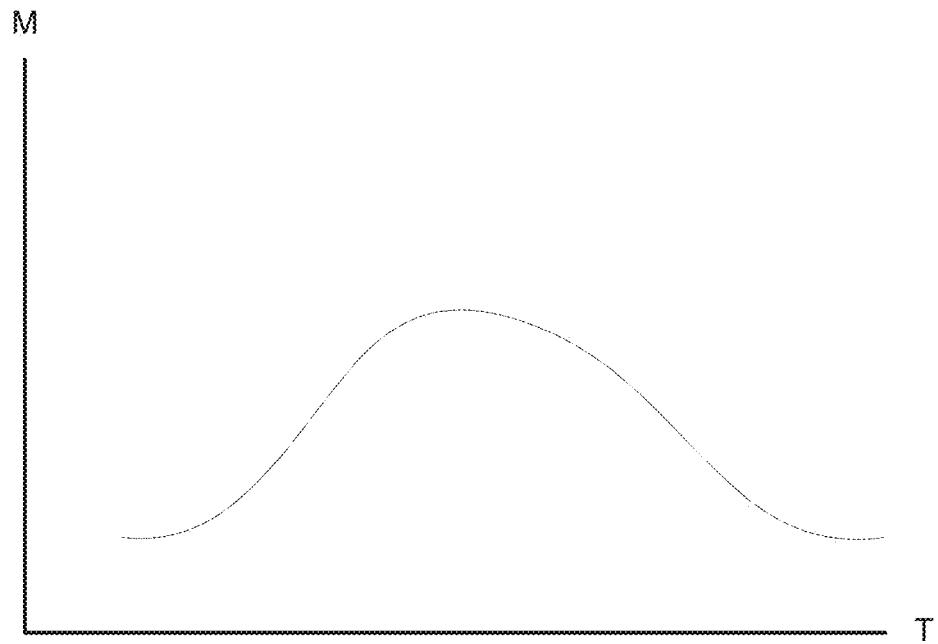
FIGS. 9A and 9B illustrate waveforms generated form data collected from the device.
Figure 9B:
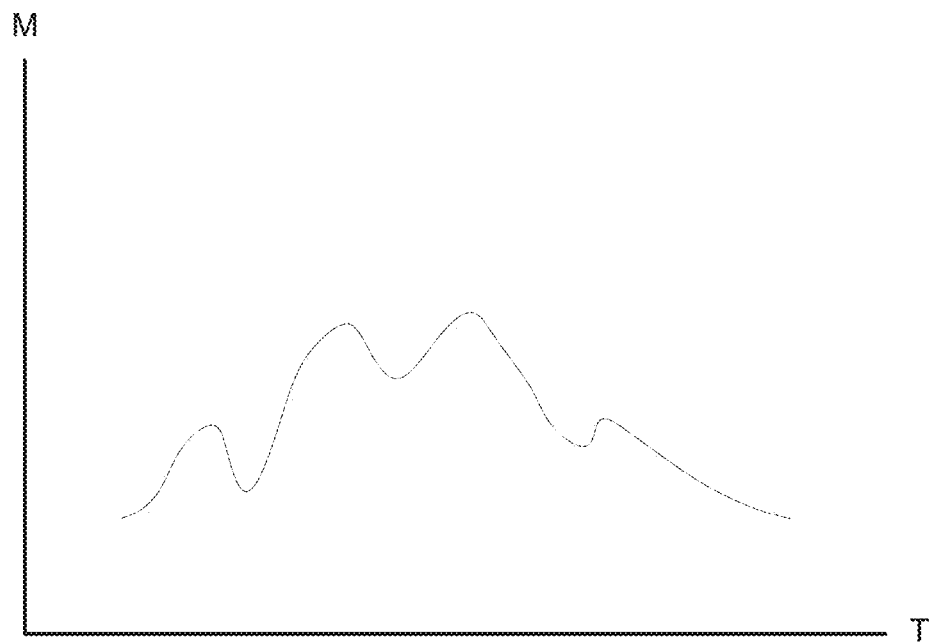

In a further arrangement, information from the device may be utilized to identify uterine contractions. FIGS. 9A and 9B illustrate monitoring of contractions or pressure within the vaginal cavity. FIG. 9A illustrates a uterine contraction associated with labor. As shown, labor contractions typically define a uniform wave that is indicative of the uterus contracting. In contrast FIG. 9B illustrates bladder spasms or other motion ways that may be monitored within the vaginal cavity. Accordingly, by monitoring such motion or pressure characteristics the device may compare a waveform to known waveforms to distinguish between, for example, labor contractions and other motion.

Though discussed in FIGS. 8-9B as primarily utilizing outputs from the motion sensors to identify origination of movements or vibrations, it will be appreciated that the outputs of any of the sensors may be monitored over time or otherwise mapped to the vaginal cavity. For instance, in one arrangement blood oxygen levels may be monitored by all of the sensor sets to identify differences within the vaginal cavity. If a location within the vaginal cavity shows lower blood oxygen levels/perfusion, such a lower blood oxygen level may be indicative of ischemia. Such ischemia may be the result of blood clots or other physical impediments. Accordingly, knowledge of the location of such an ischemia may allow for improved treatment thereof. In another arrangement, temperature may be mapped for the vaginal cavity. If a location within the vaginal cavity has an increased temperature, such increased temperature may be indicative of abscesses. Again, knowledge of location within the vaginal cavity may allow for more readily treating the condition. In a yet further arrangement, pressure may be monitored within the vaginal cavity to identify, for example, swelling. In such an arrangement, each sensor set may include a point pressure sensor (P). In addition, the device may include one or more strip sensors 92 (e.g., strain gauges) disposed about the interior of the annular body 20. See FIG. 8. Such strip sensors 92 typically have a greater length than the point sensors and may provide improved monitoring of swelling.

Figure 10:
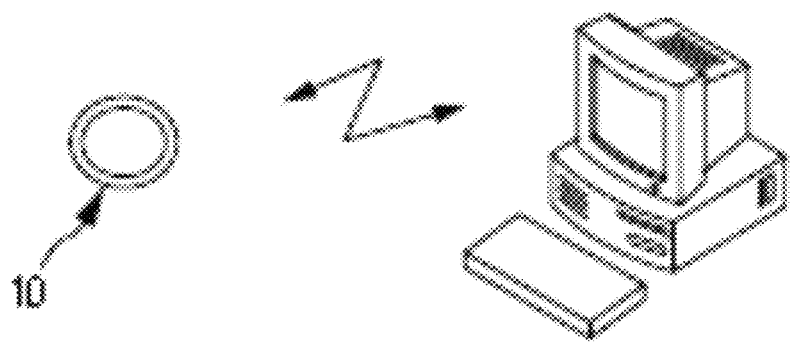
FIG. 10 illustrates a processing platform communicating with the device.

In one embodiment, the measurement device is operative to, upon wireless interrogation or direct interconnection, download accumulated measurements to a processing platform for evaluation. See FIG. 10. The processing platform or computer(s) will include one or more processors or processing units, system memory, and a bus that couples various system components including the system memory to the processor(s). The system memory may include read only memory (ROM) and random access memory (RAM). A basic input/output system (BIOS) containing the basic routines that help to transfer information between elements within computer, such as during start-up, is stored in ROM. These devices may also include internal memory such as a hard disk drive, a magnetic disk drive, and/or an optical disk drive for reading from or writing to a removable optical disk such as a CD ROM, DVD ROM or other optical media. Such interrogation may occur while the device is in use or upon removal from a user.

The drives and their associated computer-readable media provide nonvolatile storage of computer readable instructions, data structures, program modules, and other data for the processing platform. A number of program modules and/or databases may be stored on the hard disk, magnetic disk, optical disk, ROM, or RAM, including an operating system, one or more application programs, other program modules, and programs and data associated with the analysis of the monitored parameters. It will be appreciated that processing and analysis of the monitored data may be variously incorporated into hardware and/or software.

The internal measurement device 10 may be utilized to generate baseline values (e.g., diagnostic markers) that may be applicable to diagnosis of one or more therapeutic conditions including, but not limited to, hypogonadism, sexual arousal, sexual functioning, diagnose and monitor treatment response of urodynamic dysfunction (caused by tethered cord, spinal stenosis, spinal injury, etc.), labor progression or lack of progression, post-surgical recovery (bladder, vaginal, rectum), visually monitor abscess and ischemia treatment response, monitor vaginal health while on treatment for other medical conditions, monitor vaginal health while on medication(s) for other medical conditions, measure effectiveness of physical therapy for pelvic floor dysfunction, bladder and anal sphincter. In this aspect, a plurality of patients may utilize the device over an extended period to obtain one or more parameter measurements of a sample group. Such sample groups may be selected based on, for example, age, ethnicity, and/or the presence or absence of a medical condition. In any arrangement, the sample group of patients utilizes the device internally for a predetermined period of time during which the device takes periodic measurements of one or more physiological parameters. Such parameters may include, without limitation, pulse rate, blood oxygen and/or carbon dioxide levels, strain levels (e.g. constriction), temperature, motion, etc. It will be appreciated that such measurements may be direct measurements or may be inferred or calculated during processing after removal of the device or downloading of information from the device.

At the end of the set monitoring period, information from multiple patients is gathered to establish baseline characteristics for the sample group. Such baseline characteristics may be determined by various known processing techniques. Such known processing techniques may include, for example, regression analysis (or other analysis) to identify the relationship of one or more therapeutic conditions (e.g., hormone levels) to one or more physiological measurements obtained by the device. It will be further appreciated that multiple different physiological measurements may be utilized in conjunction to establish correspondences with one or more therapeutic conditions. For instance, such baseline measurements may be a combination of strain and oxygen saturation levels or other values (e.g., pH levels). Such analysis may determine baseline values or calibrations for the sample group.

In conjunction with taking measurements from such sample groups, various methods may further include obtaining one or more blood samples such that the measurements from the self-contained monitoring device(s) may be correlated to one or more components found in such blood tests. These components may include, without limitation, hormone levels, and insulin levels. It will be further appreciated that members of the sample group may be separated into subgroups based on the level of particular constituent of the blood test. In this regard, the measurement from the devices may be correlated to one or more particular hormones.

For instance, where the device is utilized to monitor hypogonadism, various blood constituents may be measured. Hypogonadism begins in both women and men at about age 30 and typically begins with a drop in the levels of androgens which in turn creates a disruption of gamete development which causes a drop in fertility and increasingly unstable and below normal levels of gonadal hormones and higher than normal levels of gonadotropins. As the gonadal hormone levels become more unstable and decline and the gonadotropins continue to rise, the ill health of hypogonadism and the strain on the other endocrine organs begins to appear.

In this regard, correlating parameter measurements from a sample group having normal levels of gonadotropins may establish a baseline reference for one or more passively measurable physiological parameters associated with pre-onset of hypogonadism. Likewise, measurements from a sample group having elevated levels of gonadotropins may be analyzed and correlated with one or more passively measurable physiological parameters associated with post-onset of hypogonadism and/or the severity or degree of the condition. In this regard, the self-contained measurement devices discussed above may be utilized to identify diagnostic markers characteristic of hypogonadism or other therapeutic conditions.

Figure 11:
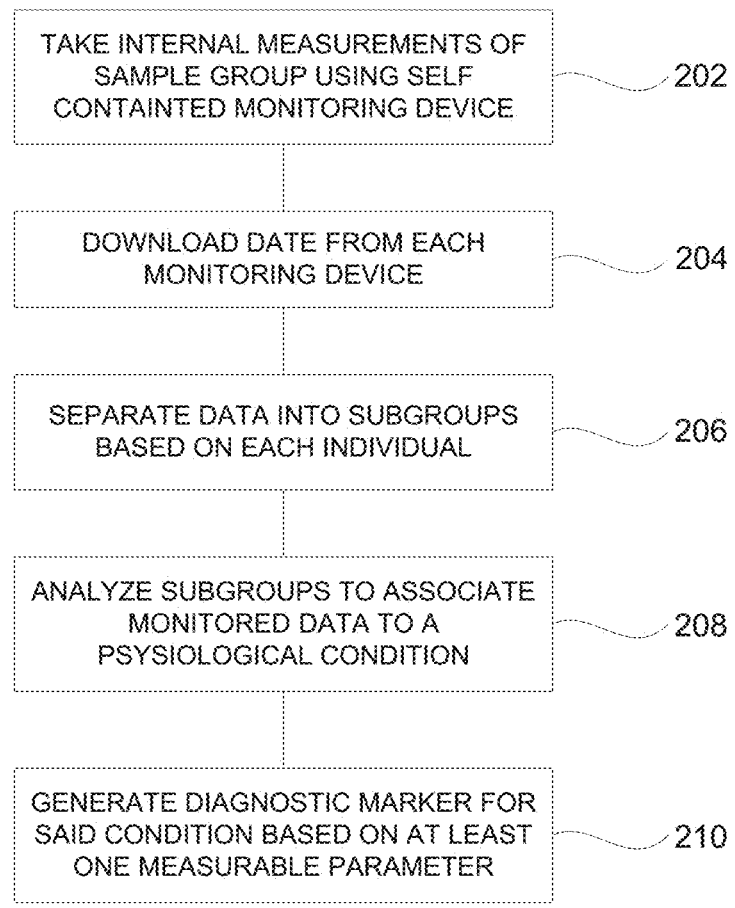
FIG. 11 illustrates one process for use with the device.

FIG. 11 illustrates a method for establishing a baseline reference for a physiological parameter. Initially, a sample group is monitored 202 for a predetermined period of time using the self-contained measurement device. The monitored parameters from the sample group is then downloaded 204 for processing. The sensor data from different subjects may then be separated 206 into subgroups based on measured levels of a particular blood constituent, hormone, etc. Further, such parameter may be determined for different locations within the body cavity. The data for each subgroup may then be analyzed 208 to determine relationships between the measured parameter and one or more locations and/or physiological conditions for the members of that group. For instance, regression analysis may be performed, which allows for modeling and analyzing several values to determine the relationship between a dependent variable (e.g., a measured hormone level, pressure, blood oxygenation, temperature) and one or more independent variables (e.g., oxygen levels, constriction strain levels, etc.). Such analysis may be done for several different subgroups to establish, for instance, relationships associated with differing levels of, for example, a particular hormone.

Figure 12:
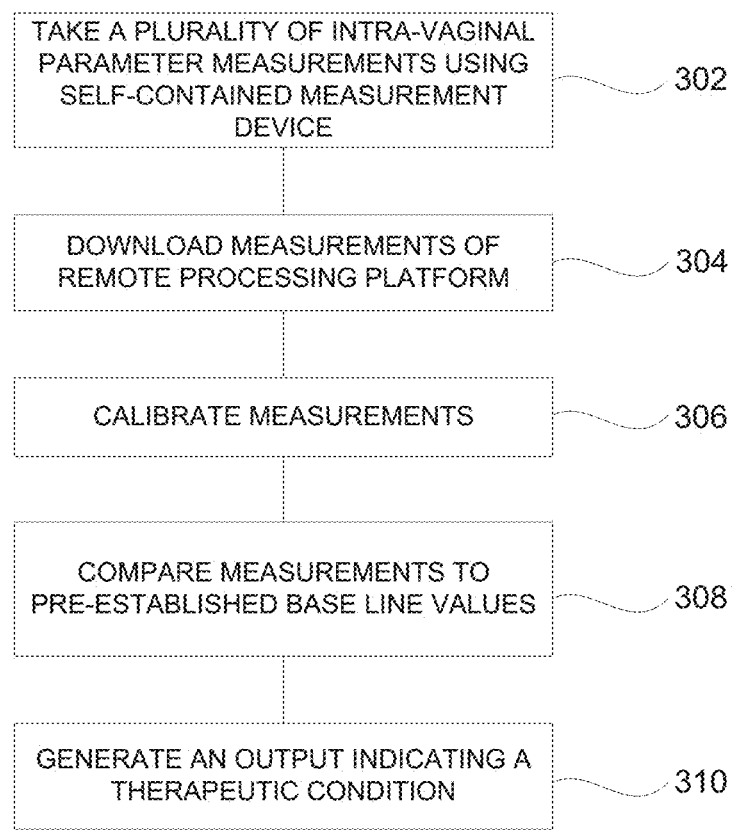
FIG. 12 illustrates another process for use with the device.

FIG. 12 illustrates a related methodology. As will be appreciated, once a baseline level and/or diagnostic marker or physiological parameter is established for a sample group, measurements from a single individual may be compared to baseline diagnostic markers or physiological parameters to provide an estimation of, for example, a level of one or more hormones and/or the presence or absence of a therapeutic condition. Initially, a user inserts the device for a predetermined period to monitor 302 physiological parameters. At the end of the measurement, the data from the measurement device is downloaded 304 to an external computer for processing. Such processing may include calibrating 308 or adjusting the sensor data, reformatting the sensor data, etc. Once downloaded and, if necessary, calibrated/adjusted, data obtained from the individual is compared 308 to pre-established baseline values. Such baseline values may be stored on a computer readable medium in, for example, a database. Finally, once compared to the baseline values, an output may be generated 310 indicating a level of one or more hormones and/or the presence or absence of a therapeutic condition. Accordingly, therapeutic treatment may be prescribed based on the output.

Once in place the device can have many uses. As noted, the sensor sets allow for mapping of the vaginal vault. That is, the sensor sets are arranged so as to accurately map the vaginal vault in 360 degrees. The 360 degree view measured over hours to days during different physiological events, menstruation, ovulation, lack of ovulation, sexual activity, mild to severe hormone deficiencies and excesses, and mild to severe nutritional deficiencies and excesses enables correlation and diagnosis of significant morbidities and perhaps even co-morbidities. Mapping 360 degrees may allow measuring the effect of multiple hormone deficiencies and excesses not just from gonadal (ovarian) hormones but also thyroid, cortisol, and potentially growth hormone.

Early diagnosis and treatment of physiological disorders often leads to faster, safer, more effective and less costly treatments. For instance, embodiments of the device will be able to detect pH disturbances before significant tissue damage and discomfort is discovered. Changes in pH can be seen in fungal and bacterial vaginal infections, different hormone imbalances and premature rupture of membranes of pregnancy. The device also has application in identifying shifts in anatomy that accompany vaginal and bladder prolapse. Earlier treatment may be able to avoid the surgery necessary when the prolapse is more advanced. Very importantly, changes in pH seen in pregnancy could mean an infection is present or amniotic fluid is leaking of which either could lead to premature rupture of membranes (PROM). Early detection of leaking amniotic fluid or infection is very important because early treatment may allow a pregnancy to continue long enough to ensure the health and safety of the fetus. The device could potentially measure the onset of labor which is very important when monitoring for early onset labor. Potentially, the device is also able to monitor fetal movements.

By mapping the vaginal vault in 3 dimensions during sexual activity with a variety of sensors, something never done before, sexual dysfunction may be identified in more specific ways thereby making treatments more effective. Stated otherwise, the data accumulated from this device will allow earlier and more effective treatments of many medical disorders as well clarify more specifics of sexual function and dysfunction.

In one application, the device will allow for monitoring spasms of the bladder associated with overactive bladder conditions. That is, the strain gages may allow for determining if the bladder is actually full and/or emptied. Likewise, the device may permit associating this condition with causation events (e.g., pH). In such an arrangement, a user could, for instance, infuse electrolytes that cause the condition. In a further embodiment, the device may be operative to provide electrical stimulation to alleviate such spasms.

In another embodiment, the device may be utilized in rectal or colon applications. In such an embodiment, the device may be an elongated device. One potential application in such an embedment is the diagnosis of Hirschsprung's disease (HD), which is a disorder of the abdomen that occurs when part or all of the large intestine or antecedent parts of the gastrointestinal tract have no nerves and therefore cannot function. In Hirschsprung's disease, part of the colon lacks these nerve bodies that regulate the activity of the colon. The affected segment of the colon cannot relax and pass stool through the colon, creating an obstruction. The most common treatment of this disease is the removal of the section of the rectum or colon lacking nerve function. The presented device may be utilized to identify the affected section. For instance, the accelerometers may identify section of the rectum/colon that lack movement.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

The invention claimed is:

1. A self contained physiological monitoring device adapted for temporary disposition within a vaginal cavity free of connection outside of the vaginal cavity, comprising:
 a toroidal body adapted for insertion into the vaginal cavity free of connection outside of the vaginal cavity;
 a battery attached to said toroidal body;
 a memory device attached to said toroidal body; and a control circuit attached to said toroidal and operatively connected to said battery and said memory device, wherein said battery, said memory device, and said control circuit are disposed within the vaginal cavity when said toroidal body is inserted within the vaginal cavity;

at least three sensors mounted at different locations about a periphery of said toroidal body, each said sensor being operatively connected to said battery and said control circuit, wherein each said sensor is operative to generate at least one sensor output of at least one physiological parameter for adjacent tissue;

at least three accelerometers mounted at different locations about the periphery said toroidal body, said accelerometers being operative to generate vector outputs for receipt by said control circuit;

wherein said control circuit is operative to:

utilize said vector outputs from said at least three accelerometers to determine an angular orientation of said toroidal body relative to the vaginal cavity wherein a first portion of said toroidal body is identified as being proximate to the posterior fornix of the vaginal cavity and a second portion of said toroidal body is identified as being proximate to the anterior fornix of the vaginal cavity;

determine a location of each said sensor about said periphery of said toroidal body relative to different regions of the vaginal cavity based on the angular orientation of the toroidal body relative to the vaginal cavity, wherein said sensors outputs are mapped to the different regions of the vaginal cavity; and store the at least one sensor output from said sensors to the memory device connected to the toroidal body.

2. The device of claim 1, further comprising:
at least one reservoir chamber mounted proximate to the body, wherein the reservoir chamber administers one or more therapeutic agents.

3. The device of claim 2, further comprising:
a plurality of reservoir chambers mounted at said different angular locations about said toroidal body.

4. The device of claim 3, wherein said control circuit is operative to administer an agent from at least one of said plurality of reservoir chambers based on said angular orientation.

5. The device of claim 1, wherein said sensors are equally angularly spaced about said toroidal body.

6. The device of claim 5, wherein said accelerometer and said sensors are co-located at said different locations.

7. The device of claim 1, wherein said accelerometers comprise three-axis accelerometers.

8. The device of claim 1, wherein said control circuit is operative to calculate said angular orientation based on an estimated plane of the vaginal cavity when a user is disposed in known orientation.

9. The device of claim 1, further comprising:
a wireless interface operatively connected to the control circuit, wherein the wireless interface is at least operative to transmit data from the memory device.

10. The device of claim 1, wherein each sensor set comprises at least two of:

a temperature sensor;

a pH sensor;

a strain gauge; and a pulse oximetry sensor.

11. A method for monitoring physiological parameters within a vaginal cavity, comprising:

inserting a measurement device having a toroidal body within a vaginal cavity of a user, wherein said measurement device is inserted within the vaginal cavity free of external connection outside the vaginal cavity;

positioning the user having the vaginally inserted measurement device in a known position, wherein a vaginal cavity of said user is substantially disposed in a known plane;

using vector signals from accelerometers disposed at three or more different positions about a periphery of said toroidal body of the measurement device to identify an angular orientation of said toroidal body relative to the vaginal cavity, wherein a first portion of said toroidal body is identified as being proximate to the posterior fornix of the vaginal cavity and a second portion of said toroidal body is identified as being proximate to the anterior fornix of the vaginal cavity;

based on said angular orientation, determining positions of sensors, disposed at different positions about the periphery of said toroidal body, relative to said vaginal cavity;

measuring at least one physiological parameter of tissue adjacent to each sensor;

mapping said at least one physiological parameter measured by each of said sensors to different locations within the vaginal cavity; and storing said at least one physiological parameter as mapped to said different locations within the vaginal cavity to a memory device attached to said toroidal body and disposed within the vaginal cavity.

12. The method of claim 11, further comprising:
utilizing said motion signals to classify contractions or spasms.

13. The method of claim 12, wherein classifying said contractions or spasms further comprises:
utilizing said motion signals to identify an origination location of said contractions or spasms.

14. The method of claim 12, further comprising:
administering a controlled dosage volume of a therapeutic agent to one of said different location within the vaginal cavity from a reservoir supported by said toroidal body and disposed proximate to said location.

15. The method of claim 11, further comprising:
processing the physiological parameter measurements for different locations in the vaginal cavity with predetermined parameter measurements for said different locations to identify differences at one or more of said different locations.

* * * * *